United States Patent [19]

Jung et al.

[11] Patent Number: 5,220,003
[45] Date of Patent: Jun. 15, 1993

[54] PROCESS FOR THE SYNTHESIS OF 2',3'-DIDEOXYNUCLEOSIDES

[75] Inventors: Michael E. Jung, Los Angeles, Calif.; John M. Gardiner, Birmingham, England

[73] Assignee: The Regents of the University of California, Oakland, Calif.

[21] Appl. No.: 677,500

[22] Filed: Mar. 29, 1991

[51] Int. Cl.$^5$ .................. C07H 19/073; C07H 1/173
[52] U.S. Cl. ............................ 536/27.11; 536/27.14; 536/28.54; 536/28.2
[58] Field of Search ............................ 536/23, 24, 26

[56] References Cited

U.S. PATENT DOCUMENTS

| | | | |
|---|---|---|---|
| 4,471,130 | 9/1984 | Katsuki et al. | 549/523 |
| 4,594,439 | 6/1986 | Katsuki et al. | 549/523 |
| 4,724,232 | 2/1988 | Rideout et al. | 514/50 |
| 4,780,453 | 10/1988 | Rideout et al. | 514/50 |
| 4,818,538 | 4/1989 | Rideout et al. | 424/436 |
| 4,818,750 | 4/1989 | Rideout et al. | 514/50 |
| 4,828,838 | 5/1989 | Rideout et al. | 424/451 |
| 4,833,130 | 5/1989 | Rideout et al. | 514/50 |
| 4,837,208 | 6/1989 | Rideout et al. | 514/50 |
| 4,847,244 | 6/1989 | Rideout et al. | 514/50 |
| 4,857,511 | 8/1989 | Rideout et al. | 514/50 |
| 4,874,609 | 10/1989 | Rideout et al. | 424/85.4 |
| 4,874,751 | 10/1989 | Beacham et al. | 514/50 |

FOREIGN PATENT DOCUMENTS 0287215 10/1988 European Pat. Off.

OTHER PUBLICATIONS

Koll et al., "Preparation of (R,S)-2,7-dioxabicyclo[2.2.1]heptane," *Chem. Ber.*, 111, 2913-2918 (1978).

Fleet et al., "Methyl 5-tert-butyldiphenylsilyl-2-deoxy-α,β-D-threo-pentofuranoside as a Divergent Intermediate for the Synthesis of Substituted-2', 3'-dideoxyucleosides: Synthesis of 3'-Azido-3'-deoxythymidine, 3'-Deoxy-3'-fluorothymidine and 3'-Cyano-3'-deoxythymidine," *Tetrahedron*, 44(2), 625-636 (1988).

Horwitz et al., "Nucleosides. V. The Monomesylates of 1-(2'-Deoxy-β-D-lyxofuranoxyl)thymine," *J. Org. Chem.*, 29, 2076-2078 (1964).

Lemieux et al., "Anomeric Deoxy and Unsaturated Methyl Pentofuranosides and Pentopyranosides," *Can. J. Chem.*, 47(23), 4413-4426 (1969); *Chem. Abstr.*, 72, p. 344, Abstr. No. 21852f, (1970); only Abstract provided.

Zaitseva, et al., *Aminonucleosides and Their Derivatives XI. Synthesis of 3'-amino-2', 3'-Dideoxynucleoside 5'-Triphosphates*, Bioorganicheskaya Khimiya, May 1984, vol. 10, No. 5, pp. 369-378.

Dyatkina, et al., *Aminonucleosides and Their Derivatives XIV. General Method of Synthesizing . . .* , Bioorganicheskaya Khimiya, Aug. 1986, vol. 12, No. 8, pp. 563-568.

Horwitz, eta l., *Nucleosides V. The Monomesylates of 1-(2'-Deoxy-β-D-lyxofuranosyl)thymine*, J. Org. Chem., vol. 29, 1964, pp. 2076-2078.

Jung, et al., *Synthetic Approaches to 3'-Azido-3'-deoxythymidine and Other Modified Nucleosides*, J. Org. Chem., vol. 56, 1991, pp. 2614-2615.

Hager, et al., *Cyclization Protocols for Controlling the Glycosidic Stereochemistry of Nucleosides. Application to . . .* , J. Am. Chem. Soc., vol. 113, 1991, pp. 5117-5119.

Jung, et al., *Preparation of Modified Nucleosides from Glucosamine: Rapid and Efficient Formal Total Synthesis of Several . . .* , J. Chem. Soc. Chem. Commun., 1990, pp. 84-85.

Farina, et al., *A New Synthesis of 2',3'-Dideoxynucleosides for AIDS Chemotherapy*, Tetrahedron Letters, vol. 29, 1988, pp. 1239-1242.

Okabe, et al., *Synthesis of the Dideoxynucleosides ddC and CNT from Glutamic Acid, Ribonolactone, and Pyrimidine Bases*, J. Org. Chem., vol. 53, 1988, pp. 4780-4786.

(List continued on next page.)

*Primary Examiner*—Johnnie R. Brown
*Assistant Examiner*—L. Eric Crane
*Attorney, Agent, or Firm*—Christie, Parker & Hale

[57] ABSTRACT

Methods are provided for preparing 3'-substituted-2',3'-dideoxynucleosides, and the like, from non-carbohydrate, non-nucleoside starting materials.

8 Claims, No Drawings

OTHER PUBLICATIONS

Okabe, et al., *Synthesis of 1-(2,3-Dideoxy-2-fluoro-β-D-threopentofuranoxyl)cytosine (F-ddC). A Promising agent for...*, J. Org. Chem., vol. 56, 1991, pp. 4392–4397.

Mansuri, et al., *Preparation of the Geometric Isomers of DDC, DDA, D4C and D4T as Potential Anti-HIV Agents*, Bioorg. Med. Chem. Letters, vol. 1, No. 1, 1991, pp. 65–68.

Robins, *Synthetic Antiviral Agents*, Chem. Eng. News, vol. 64, No. 4, 1986, pp. 28–40.

Makin, et al., *Enantioselective Epoxidation of the Acetals of Unsaturated Hydroxy Aldehydes. 2-Deoxy-L-Ribose*, J. Org. Chem. USSR, vol. 20, 1984, pp. 189–190 (Engl. Transl.).

Hughes, et al., *Total Synthesis of 3(S)-Carboxy-4(S)-hydroxy-2,3,4,5-tetrahydropyridazine, an Unusual Amino Acid Constituent...*, J. Org. Chem., vol. 54, 1989, pp. 3260–3264.

Maruoka, et al., *A Highly Regio- and Stereoselective Ring-Opening of 2,3-Epoxy Alcohols with Trimethylsilyl Azide-Diethylaluminum...*, Chem. Letters, 1985, pp. 599–602.

Caron, et al., *Ti(O-i-Pr)$_4$-Mediated Nucleophilic Openings of 2,3-Epoxy Alcohols. A Mild Procedure for Regioselective Ring-Opening*, J. Org. Chem., vol. 50, 1985, pp. 1557–1560.

Lemieux, et al., *Anomeric deoxy and unsaturated methyl pentofuranosides and pentopyranosides*, Can. J. Chem., vol. 47, No. 19, 1969, pp. 4413–4426.

Niedballa, et al., *A General Synthesis of N-Glycosides. I. Synthesis of Pyrimidine Nucleosides*, J. Org. Chem., vol. 39, No. 25, 1974, pp. 3654–3660.

Vorbrüggen, et al., *Nucleosides Synthesis with Trimethylsilyl Triflate and Perchlorate as Catalysts*, Chem. Ber., vol. 114, 1981, pp. 1234–1255.

Samukov, et al., *Synthesis of 2′,3′-Dideoxynucleosides*, Bioorganicheskaya Khimiya, vol. 9, 1983, p. 52 (Engl. Transl.).

PROCESS FOR THE SYNTHESIS OF 2',3'-DIDEOXYNUCLEOSIDES

ACKNOWLEDGEMENT OF GOVERNMENT SUPPORT

This invention was made with government support under Grant No. AI-26692 awarded by the National Institutes of Health. The government has certain rights in the invention.

FIELD OF THE INVENTION

This invention is directed to processes for making 2',3'-dideoxynucleosides, 2',3'-dideoxy-2',3'-didehydronucleosides, 3'-substituted-dideoxynucleosides, and the like.

BACKGROUND OF THE INVENTION

Modified nucleosides (e.g., 3'-substituted, deoxy-, dideoxy-, and dideoxy-didehydronucleosides) are known to exhibit actual or potential activity against a variety of contagions, anti-tumor activity, and/or usefulness as chemotherapeutic agents. For example, 3'-azido-3'-deoxythymidine (AZT) is effective in treating infection by the HTLV III virus (see, e.g., U.S. Pat. No. 4,724,232 to Rideout, et al.), feline leukemia virus (U.S. Pat. No. 4,780,453 to Rideout, et al.) and gram-negative bacteria (U.S. Pat. No. 4,874,751 to Beacham III, et al.). In order to make these compounds available on a large scale, chemists have worked for years on the development of new methods for their preparation.

The synthesis of AZT is illustrative. AZT was prepared by Horowitz in 1964 using a six-step process starting with the naturally occurring nucleoside, thymidine. J. R. Horowitz, et al., *J. Org. Chem.* 1964, 20, 2076. A shorter route is described in several U.S. patents to Rideout, et al. (assigned to Burroughs-Wellcome Co.) and entails converting thymidine to 2,3'-anhydrothymidine, followed by reaction with sodium azide to give AZT. A similar route was reported by a Russian group in 1984. V. E. Zaitseva, et al., *Bioorg. Khim.* 1984, 10, 670.

A different approach, starting with a sugar, was described by Fleet in 1988. G. W. J. Fleet, et al. *Tetrahedron* 1988, 44, 625 (incorporated herein by reference). Fleet's synthesis entails conversion of D-xylose to methyl 5-O-tert-butyldiphenylsilyl-2-deoxy-$\alpha,\beta$-D-threo-pentofuranoside, reaction with sodium azide to give an azido-pentofuranoside, and subsequent coupling with silylated thymine in the presence of trialkylsilyl triflates to give AZT. A similar route, based on the condensation of methyl-3-azido-2,3-dideoxy-5-O-p-toluyl-$\alpha,\beta$-D-ribofuranoside with silylated thymine (or other heterocyclic bases) was described by the same Russian group in 1986 N. B. Dyatkina, et al., *Bioorg. Khim.* 1986, 12, 1048.

Other modified nucleosides have been prepared. See, e.g., European Patent No. 187,215 to Rideout, et al. (4-deoxy-AZT, a pro-drug of AZT); M. E. Jung, et al., *J. Chem. Soc. Chem. Commun.* 1990, p. 84 (2'-deoxy C-nucleosides); and R. K. Robins, *Chem. Eng. News* 1986, 64 (4), and references therein (general overview of synthetic antiviral agents).

To date, nearly every approach to the synthesis of modified nucleosides has begun with chemical compounds such as naturally occurring nucleosides or sugars. With limited exception, most of these material are quite expensive. Thymidine, for example, costs approximately $6.60 per gram. Accordingly, a need exists for an inexpensive, straightforward process for making modified nucleosides. The present invention fulfills that need.

SUMMARY OF THE INVENTION

This invention provides novel synthetic routes to modified nucleosides such as 3'-azido-3'-deoxythymidine (AZT), dideoxycytidine (ddC), dideoxydidehydrothymidine (d$_4$T), and the like, starting with simple organic compounds that are neither carbohydrates nor nucleosides. Asymmetry is introduced at what becomes the 3' and 4' positions by using a Sharpless epoxidation.

More specifically, crotonaldehyde, or a silyl enol ether derivative thereof, is converted to a modified ribofuranoside, and a purine or pyrimidine base is coupled thereto to yield the modified nucleoside. Key intermediates include an epoxy alcohol and various diols. The modified ribofuranosides are formed by treating the diols with dilute acid.

In an exemplary embodiment of the invention, D-3'-azido-3'-deoxythymidine (AZT) is synthesized from crotonaldehyde by the following steps:

(a) silylation of crotonaldehyde to yield a silyl enol ether; (b) condensation of the silyl enol ether with trimethyl orthoformate to yield an enal; (c) reduction of the enal to yield an allylic alcohol; (d) Sharpless epoxidation of the allylic alcohol to yield an epoxy alcohol of desired configuration; (e) reaction of the epoxy alcohol with diethylaluminum fluoride and azidotrimethylsilane to yield a five-carbon azido diol; (f) cyclization of the azido diol, using dilute acid, to yield a 3-azido-2,3-dideoxyribofuranoside; and (g) preparation of AZT by (i) protecting the primary hydroxyl group, (ii) reacting the hydroxy-protected azido-ribofuranoside with silylated thyine, and (iii) de-protecting the hydroxyl group to yield AZT.

Dideoxycytidine (ddC) is prepared in a similar manner: crotonaldehyde is converted to the epoxy alcohol as in the above paragraph, and the epoxy alcohol is converted to 5,5-dimethoxypentane-1,2-diol by reaction with diisobutylaluminum hydride. The diol is then converted to a 2,3-dideoxyribofuranoside by treatment with dilute acid. Protection of the hydroxyl group, treatment with silylated cytosine, and de-protection yields ddC.

Dideoxydidehydrothymidine (d$_4$T) is prepared by converting the above-mentioned epoxy alcohol to 3-thiophenoxy-5,5-dimethoxypentane-1,2-diol, using thiophenol and a metal catalyst. The diol is then cyclized using dilute acid, and the resulting 3-thiophenoxy-2,3-dideoxyribofuranoside is hydroxy-protected, then oxidatively eliminated to obtain a 2,3-dideoxy-2,3-didehydroribofuranoside using MCPBA or NaIO$_4$. Coupling with silylated thymine yields d$_4$T.

The present invention also provides an inexpensive route to L-2'-deoxynucleosides, which in turn are polymerizable to enantio-DNA ("anti-sense" DNA), which is presently being investigated for its ability to prevent gene expression. L-2'-deoxynucleosides are prepared by converting crotonaldehyde to an enantiomer of the above-mentioned epoxy alcohol, converting the epoxy alcohol to a hydroxy-protected L-ribofuranoside, and coupling the L-ribofuranoside with a purine or pyrimidine base in a manner similar to that described above.

By starting with crotonaldehyde, an inexpensive ($14/liter) commodity chemical, the present invention provides a low-cost route to AZT and other modified nucleosides. The invention is also marked by great versatility. Preparation of 3'-substituted nucleosides, 2',3'- dideoxynucleosides and 2′,3′-dideoxy- 2′,3′-didehydronucleosides from crotonaldehyde proceeds in each case by formation of a common intermediate, namely, an epoxy alcohol. Similarly, the synthesis of AZT described herein is equally useful in preparing modified nucleoside analogues of AZT, e.g., AZI, AZU, AZC, and the like, since the base is added after the furanoside is prepared.

DETAILED DESCRIPTION

The present invention provides new processes for preparing modified nucleosides. As used herein, the term "modified nucleoside" means a compound structurally analogous to a naturally occurring nucleoside—adenosine, cytidine, guanosine, thymidine, uridine, and the like—i.e., a compound comprising a purine or pyrimidine base, or derivative thereof, linked to a ribose, deoxyribose, dideoxyribose, or similar moiety. In particular, the term includes 3′-substituted-2′,3′-dideoxynucleosides, 2,,3,-dideoxynucleosides, and 2′,3′-dideoxy-2′,3′-didehydronucleosides. Both L- and D-enantiomers are included.

Modified nucleosides are prepared by first converting a silyl enol ether, (1,3-butadien-1-yl)oxytrimethylsilane (commercially available from Aldrich or prepared from crotonaldehyde) to an epoxy alcohol having the desired configuration. For D-modified nucleosides, the epoxy alcohol is (2R,3R) 3-(2,2-dimethoxyethyl)oxiranemethanol:

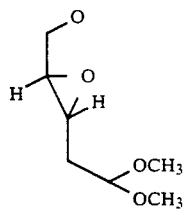

For L-modified nucleosides, the epoxy alcohol is (2S,3S) 3-(2,2-dimethoxyethyl)oxiranemethanol:

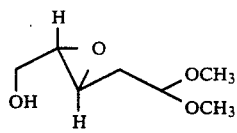

The epoxy alcohol is prepared in the following manner: A solution of crotonaldehyde is heated with trimethylsilyl chloride, zinc chloride and triethylamine, in benzene, to obtain a mixture of (E) and (Z) (1,3-butadien-1-yl)oxytrimethylsilane:

The silyl enol ether is mixed with trimethyl orthoformate and zinc chloride and heated in dichloromethane to obtain 5,5-dimethoxypent-2-enal:

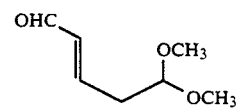

The enal is dissolved in diethyl ether and reduced with diisobutylaluminum hydride (DIBAL) to obtain 5,5-dimethoxypent-2-en-1-ol as a mixture of and Z isomers, in which the desired isomer greatly predominates (>95%):

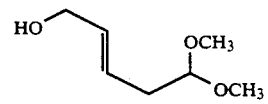

Sharpless epoxidation of the allylic alcohol yields the epoxy alcohol, with stereoconfiguration being controlled by the particular enantiomer of tartrate used. More specifically, the allylic alcohol is added, with tert-butylhydroperoxide, to a cooled (−20° C.) solution of D-(−)-diisopropyl tartrate and titanium (IV) tetraisopropoxide to obtain (2R,3R) 3-(2,2-dimethoxyethyl)oxiranemethanol (>95% enantiomeric excess). Alternatively, (2S,3S) 3-(2,2-dimethoxyethyl)oxiranemethanol is obtained by using L-(+)-diisopropyl tartrate.

The epoxy alcohol is converted to a 3-substituted-2,3-dideoxyribofuranoside, a 2,3-dideoxyribofuranoside, or a 2,3-dideoxy-2,3-didehydroribofuranoside by a series of steps that will now be described.

3′-Substituted-2′3′-Dideoxynucleosides

A mixture of the epoxy alcohol (2R,3R) 3-(2,2-dimethoxyethyl)oxirane-methanol and azidotrimethylsilane in dichloromethane is reacted with diethylaluminum fluoride to obtain (2S,3S) 3-azido-5,5-dimethoxypentane1,2-diol:

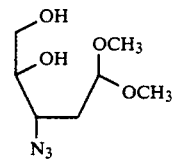

The azido diol is dissolved in dichloromethane and treated with dilute acid, e.g., 1.5% hydrochloric acid in methanol, to obtain a mixture of two anomers—methyl α- and β-D-3-azido-2,3-dideoxyribofuranoside:

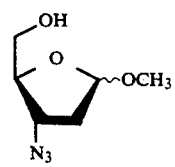

By keeping the concentration of the azido diol low, cyclization to the ribose (five-membered ring) predominates over cyclization to the hexose (six-membered ring).

The above-described ribofuranoside is converted to a modified nucleoside, i.e., a 3′-azido-2′,3′-dideoxynucleoside, using Vorbrüggen or Hilbert-Johnson technology (i.e., coupling with a silylated base in the presence of a trialkylsilyl triflate, as described in the Fleet reference, supra.). First, the primary hydroxyl group is protected by reacting the anomeric mixture of methyl α- and β-D-3-azido-2,3-dideoxy-ribofuranoside with tert-butyldiphenylsilyl chloride (TPSCl) in DMF, along with imidazole, to obtain a hydroxy- protected D-3-azido-2,3-dideoxyribofuranoside, e.g., methyl α- and β-D-3-azido-2,3-dideoxy-5-[(1,1-dimethylethyl)diphenylsilyloxy]ribofuranoside:

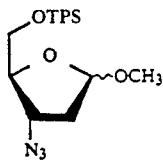

The hydroxy-protected D-3'-azido-2,3-dideoxyribofuranoside is reacted with a silylated purine or pyrimidine base, in the presence of a trialkylsilyl triflate, and the hydroxyl group on the primary carbon is deprotected, to obtain a D-3'-azido-2,3-dideoxynucleoside of the formula:

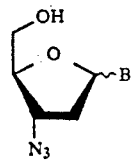

wherein B is a purine or pyrimidine base.

As desired, the modified nucleoside is then separated into its α and β anomers

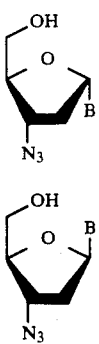

by flash chromatography or similar technique. (Optionally, the hydroxy-protected, as well as the unprotected 3-azido-2,3-dideoxyribofuranoside are separated into α- and β-anomers using silica gel chromatography or TLC prior to conversion to the nucleoside. Regardless of whether a pure anomer or mixture is used, one obtains an α β mixture of the nucleoside. Typically, only one anomer (usually β) is bioactive.)

Methyl α- and β-L-3'-azido-2',3'-dideoxynucleosides are prepared in a manner identical to that just described, except that (2S,3S) 3-(2,2-dimethoxyethyl)oxiranemethanol is employed as the epoxy alcohol.

In addition to 3'-azido-2',3'-dideoxynucleosides, other 3'-substituted-2',3'-dideoxynucleosides are prepared in accordance with the present invention by substituting other nucleophiles, e.g., -halo, -cyano, -thioalkyl, -phosphono derivatives, and the like, for azide in the conversion of the epoxy alcohol to the diol.

2'3'-Dideoxynucleosides

The epoxy alcohol (2R,3R) 3-(2,2-dimethoxyethyl)oxiranemethanol is reacted with diisobutylaluminum hydride, in benzene, to obtain 5,5-dimethoxypentane-1,2-diol:

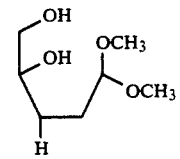

The diol is dissolved in dichloromethane and treated with dilute acid to obtain a dideoxyribofuranoside, i.e., methyl α- and β-D-2,3-dideoxyribofuranoside:

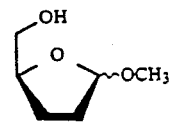

The dideoxyribofuranoside is converted into a 2',3'-dideoxynucleoside having the formula:

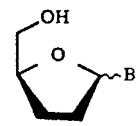

by the same process used in converting a 3-azido-2,3-dideoxyribofuranoside to a 3'-azido-2',3'-dideoxynucleoside. Thus, dideoxycytidine (ddC) is prepared by protecting the hydroxyl group on the primary carbon of the dideoxyribofuranoside, reacting the resulting hydroxyprotected dideoxyribofuranoside with silylated cytosine, and de-protecting the hydroxyl group to obtain ddC.

As desired, a 2'3'-dideoxynucleoside prepared in the above manner is resolved into α- and β-anomers

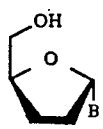
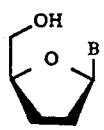

using flash chromatography or a similar technique.

2'3'-Dideoxy-2'3'-Didehydronucleosides

The epoxy alcohol (2R,3R) 3-(2,2-dimethoxyethyl)oxiranemethanol is reacted with thiophenol in the presence of a metal catalyst to obtain 3-thiophenoxy-5,5-dimethoxy pentane-1,2-diol:

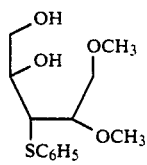

The thiophenoxy diol is dissolved in dichloromethane and treated with dilute acid (in a manner similar to that described above for the diol and the azido diol) to obtain a 3-thiophenoxy-2,3-dideoxyribofuranoside having the formula:

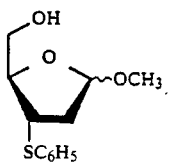

The 3-thiophenoxy-2,3-dideoxyribofuranoside is treated with tert-butyldiphenylsilyl chloride (TPSCl) or a similar reagent to obtain a hydroxy-protected 3-thiophenoxy-2,3-dideoxyribofuranoside, which is reacted with a per-acid such as, but not limited to, meta-chloroperbenzoic acid (MCPBA), or $NaIO_4$ to obtain a hydroxyprotected 2,3-dideoxy-2,3-didehydroribofuranoside having the formula:

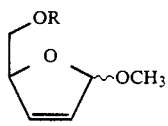

where R is a protecting group (e.g., TPS).

The hydroxy-protected 2,3-dideoxy-2,3-didehydroribofuranoside is converted to a 2,3-dideoxy-2,3-didehydronucleoside:

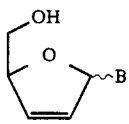

wherein B is a purine or pyrimidine base, in a manner similar to that described above, i.e., it is reacted with a silylated base in the presence of a trialkylsilyl triflate and then de-protected. For example, dideoxydidehydrothymidine ($d_4T$) is prepared by reacting the above-described hydroxy-protected 2,3-dideoxy-2,3-didehydroribofuranoside with silylated thymine, and de-protecting the hydroxyl group on the primary carbon to obtain $d_4T$.

Those skilled in the art will appreciate that the compounds described above—3'-substituted-2'3'-dideoxynucleosides; 2',3'-dideoxynucleosides; 2',3'-dideoxy-2'3'didehydronucleosides; the modified ribofuranoside precursors thereof, and the like—can be prepared as both the D- and L-enantiomers, and that the compounds are separable into α- and β-anomers.

L-2'-deoxynucleosides

The present invention also provides a synthetic route to L-2'-deoxynucleosides, which can be polymerized to enantio-DNA.("anti-sense" DNA). Synthesis of L-2'-dideoxynucleosides proceeds as follows: The epoxy alcohol (2S,3S) 3-(2,2-dimethoxyethyl)oxiranemthanol is reacted with benzyl alcohol in the presence of titanium (IV) tetraisopropoxide to obtain 3-benzyloxy-5,5-dimethoxypentane-1,2-diol:

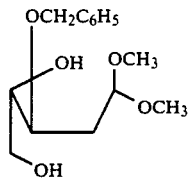

The benzyloxy diol is dissolved in dichloromethane and treated with dilute acid (in a manner similar to that described above) to obtain a 2,3-deoxy-3-0-benzyl-ribofuranoside having the formula

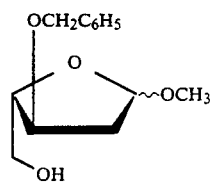

This compound is treated with benzyl bromide, in the presence of a base, to obtain a hydroxy-protected L-ribofuranoside having the formula

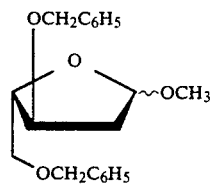

The hydroxy-protected L-ribofuranoside is converted to an L-2'-deoxynucleoside using Vorbrüggen or Hilbert-Johnson technology, i.e., the compound is treated with a silylated base in the presence of a trialkylsilyl triflate, and both hydroxyl groups de-protected to obtain a mixture of α- and β-anomers of an L-2'-deoxynucleoside:

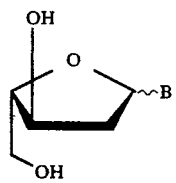

wherein B is a purine or pyrimidine base.

Such a nucleoside is separated into α- and β-anomers by flash chromatography or similar technique. The β-anomer has the formula:

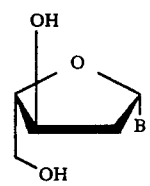

and is polymerized into enantio-DNA using known techniques.

The following examples describe in detail syntheses illustrative of the present invention. It will be apparent to those skilled in the art that many modifications, both of material and methods, may be practiced without departure from the purpose and intent of this disclosure.

EXAMPLE 1

(E) and (Z) (1.3-butadien-1-yl)oxytrimethylsilane

To a solution of crotonaldehyde (31.8 g, 0.454 mole) and triethylamine (51.4 g, 1.1 eq) in benzene at 25° C., was added hydroquinone (0.95 g) and zinc chloride (0.75 g) rapidly with efficient stirring. This was followed by the addition of freshly distilled trimethylsilyl chloride (46 ml, 0.9 eq) over 1–2 minutes, whereupon a white precipitate rapidly formed. After stirring the mixture for 30 minutes at 25° C., a further 0.2 eq of trimethylsilyl chloride were added. The reaction was then warmed to 70° C. and stirred at this temperature for 12 hours. It was then cooled to 0° C., quenched by addition of saturated aq. $NaHCO_3$ (75 ml), poured into a separatory funnel, and the organic layer separated. The aqueous layer was extracted with further portions of benzene (3×50 ml), the organic extracts combined, washed with 10% $KHSO_4$, and the benzene removed in vacuo to leave a dark brown liquid. Distillation through a short Vigreaux column yielded 28.4 g (46%) of pure 1-trimethylsilyloxy-1,3-butadiene as a colorless liquid (bp 78°–80° C./68 mm Hg). $^1H$ NMR (200 MHz, $CDCl_3$): δ 6.66(1H,d,J=11.9 Hz), 6.35(1H,dt,J=17.1, 10.6Hz), 5.84(1H,t,J=11.4 Hz), 5.11(1H,dd,J=16.8, 1.8 Hz), 4.94(1H,dd,J=10.3, 1.8 Hz), 0.37(9H, s).

$^{13}C$ NMR (50 MHz,$CDCl_3$): δ144.56, 133.22, 114.44, 111.96, −0.53.

EXAMPLE 2

(E) 5,5-Dimethoxypent-2-enal

To a mixture of 1-trimethylsilyloxy-1,3-butadiene (14.57 g, 0.1 mol) and trimethyl orthoformate (10 855 g, 0.1 mol) stirring in dichloromethane (500 ml) was added $ZnCl_2$ (1.75 g, 10% mol), and the mixture stirred vigorously at 25° C. for 18 h. The reaction mixture was then poured into saturated aq. $NaHCO_3$ (100 ml), and the organic layer collected. The aqueous layer was reextracted with dichloromethane (100 ml), the combined organic extracts dried over $MgSO_4$, and the solvents removed in vacuo. The resulting brown oil was taken up in hexane/ethyl acetate (1:1) and filtered through a pad of flash silica gel, washing through with a further 400 ml of the solvent mixture. The solvents were removed in vacuo and the crude product Kugelrohr distilled slowly (~0.4 MM Hg/100° C.) to provide the pure enal (7.065 g, 49%)

$^1H$ NMR (200 MHz, $CDCl_3$): δ 9.38(1H,d,J=7.9 Hz), 6.63(1H,dt,J=15.7, 7 Hz), 5.96(1H,ddt,J=15.8, 1.4, 7.9Hz), 4.32(1H,t,J=5.44 Hz), 3.18(6H's), 2.46(2H,ddd,J=7, 5.5, 1.4 Hz).

$^{13}C$ NMR (50 MHz, $CDCl_3$): δ 193.4, 152.3, 134.7, 102.5, 53.0, 36.1.

IR(neat): 2990, 2960, 2930, 2900, 2830, 2740, 1718 $cm^{-1}$.

EXAMPLE 3

(E) 5,5-Dimethoxypent-2-en-1-ol

To a stirring solution of the enal (5.17 g, 0.036 mol) in diethyl ether (350 ml) cooled in an ice-acetone bath was added diisobutylaluminum hydride (39 ml, 1.0 M in hexanes, 1.08 eq) in portions over 5 minutes. The solution was allowed to warm to 25° C. and was stirred a further 10 hours. The reaction was quenched by slow addition of saturated sodium chloride solution (75 ml), stirred a further 2 hours, and the organic layer separated. The aqueous layer was reextracted with ethyl acetate (2×100 ml), and the combined organic phases dried over $Na_2SO_4$, filtered, and the solvents removed in vacuo to yield 4.6 g (87%) of the crude alcohol. Chromatography on silica gel (30:1 $CH_2Cl_2$/MeOH) yields 3.6 g (70%) of the pure allylic alcohol.

$^1H$ NMR (200 MHz, $CDCl_3$): δ 5.44–5.69(2H, m), 4.29(1H,t,J=5.7 Hz), 3.78(2H,d,J=3.9 Hz), 3.22(6H's), 2.27 (2H,t,J=5.7 Hz).

$^{13}C$ NMR (50 MHz, $CDCl_3$): δ 132.3, 126.2, 103.8, 63.0, 52.8, 35.6

IR (neat): 3400 (OH), 2925, 2895, 2820 $cm^{-1}$.

EXAMPLE 4

(2R,3R) 3-(2,2-Dimethoxyethyl)oxiranemethanol

To a solution of D-(−)-diisopropyl tartrate (0.78 g, 3.33 mmol) in dichloromethane (25 ml), cooled to −20° C., was added titanium tetraisopropoxide (0.9 ml, 2.8 mmol), and the mixture stirred at −20° C. for 15 minutes. The allylic alcohol (0.4 g, 2.7 mmol) was then added as a solution in dichloromethane (10 mil) and after a further 10 minutes stirring at −20° C., t-butyl hydroperoxide (2 ml, 2.0 M, 2 eq) was added. The reaction mixture was stored in a refrigerator at −20° C. for 2 days and then quenched by addition of 30% NaOH in saturated sodium chloride. The mixture was allowed to warm to 25° C. and stirred a further 4 hours, when $MgSO_4$ (3 g) and Celite (1 g) were added, and the resultant well-stirred mixture was filtered through a pad of Celite. After removal of the solvents in vacuo, the residue was chromatographed on silica gel (30:1 $CH_2Cl_2$/MeOH), yielding the epoxy alcohol (R, R) (326 mg, 74%) as a colorless oil.

$^1H$ NMR (200 MHz, $CDCl_3$): δ 4.50(1H,dd,J=6.5, 4.9 Hz), 3.82(1H,dd,J=12.5, 2.5 Hz), 3 57 (1H,dd,J=12.5, 4.4 Hz) 3.30(3H's), 3.27(3H's), 2.98(1H,m), 2.96(1H,m), 1.83–1.90(1H,m), 1.69–1 79(1H,m).

$^{13}C$ NMR (50 MHz, $CDCl_3$): δ 102.2(d), 61.7(t), 58.3(d), 53.4(q), 52.9(q), 52.2(d), 35.2(t).

IR (neat): 3440, 2980, 2920, 2825 $cm^{-1}$.

EXAMPLE 5

(2S, 3S) 3-Azido-5,5-dimethoxypentane-1,2-diol

To a stirred mixture of the epoxy alcohol (R, R) (200 mg, 1 26 mmol) and azidotrimethylsilane (340 mg, 2.3eq) in dichloromethane (12 ml) cooled to 0° C., was added diethylaluminum fluoride (2 ml, 25% solution, 4eq), and the mixture allowed to warm to 25° C. and stir a further 48 h. The reaction was quenched by addition of saturated $NaHCO_3$ (10 ml), the organic layer collected, and the aqueous layer washed with dichloromethane (2×10 ml). The combined organic extracts were washed with brine, dried over $Na_2SO_4$, filtered and the solvents removed in vacuo. The crude diol was chromatographed on silica gel (eluting first with $CH_2Cl_2$, then with 2% MeOH/$CH_2Cl_{23}$) yielding 161.8 mg (64) of the pure azido diol.

$^1H$ NMR (200 MHz, $CDCl_3$): δ 4.56 (1H,dd,J=11.1, 4.5 Hz),3.58–3.76 (3H, m), 3.44–3.5 (1H m) 3.37 (6H s) 1.95–2.05 (1H, m), 1.73–1.87 (1H, m).

$^{13}$C NMR (50 MHz, CDCl$_3$): δ 102.4(d), 73.7 (d), 63.1 (t), 60.4 (d), 53.7 (q), 53.6 (q), 33.8 (t), IR (neat); 3440 (v br), 2920, 2825, 2100 (N$_3$, sharp) cm$^{-1}$.

EXAMPLE 6

Methyl α- and β-D-3-Azido-2,3-dideoxyribofuranoside

To a solution of 67 mg (0.33 mmol) of the azido diol in dichloromethane (60 ml) at 25 °C. was added 10 drops of approximately 1.5% HCl in aqueous MeOH, and the mixture stirred for 5 min. TLC showed complete conversion to a mixture of the anomeric products. The reaction was quenched by addition of 1 ml saturated aq. NaHCO$_3$ and vigorously stirred for 2 min. Sodium sulfate was added, the solution filtered, and the solvents removed in vacuo. Chromatography on silica gel (eluting first with CH$_2$Cl$_2$, then with 1% MeOH/CH$_2$Cl$_2$) yielded 46.8 mg (81%) of the pure mixture of the two anomeric products. Samples of the pure α or β anomer were obtained by either further silica gel chromatography or preparative TLC (eluting with 24:1 CH$_2$Cl$_2$/MeOH).

β-anomer $^1$H NMR (200 MHz, CDCl$_3$): δ 5.10 (1H,dd,J=5.4, 1.7 HZ), 4.09-4.28 (2H, m), 3.78 (1H,dd,J=12 Hz), 3.63 (1H,m,J=8.9 Hz), 3.40 (3H's,OMe), 2.52 (1H,dd,J=9.0, 3.7 Hz, OH), 2.35 (1H,ddd,J=13.9, 7 4, 1.8 Hz), 2.17 (1H,ddd,J=13.8, 6.4, 5.5 Hz).

α-anomer $^1$H NMR (200 MHz, CDCl$_3$; 5.08 (1H,dd,J=5.2, 1.4 Hz), 3 84-4.02 (3H, m), 3.69 (1H, m), 3.39 (3H's,OMe), 2.40 (1H,ddd,J=14.1, 8.7, 5.3 Hz), 2.03 (1H,ddd,J=14.2, 3.6, 1.4 Hz), 1.82 (1H,dd,J=7.9, 4.6 Hz, OH).

mixture of α- and β-anomers $^{13}$C NMR (50 MHz, CDCl$_3$): δ 105.2 (β), 104.9 (α), 85.2 (β, 82.3 (α), 63.5 (β), 62.2 (α), 60.6 (β), 59.8 (α), 55.6 (β), 55.1 (α), 39.5 (β), 39.1 (α). lit. (Fleet) $^{13}$C NMR (CDCl$_3$): δ 105.1, 104.8, 85.2, 82.5, 63.5, 62.4, 60.6, 60.0, 55.5, 55.2, 39.5, 39.2. IR (neat): 3250-3500 (v br), 2925, 2100 (v strong, sharp N$_3$), 1435, 1365, 1325, 1255, 1100, 1040 cm$^{-1}$.

EXAMPLE 7

Methyl α- and β-D-3-Azido-2,3-dideoxy-5-[(1,1-dimethylethyl)diphenylsilyloxy]ribofuranoside To a solution of the alcohol (19 mg, 0.110 mmol) and imidazole (29 mg, 4 eq) in DMF (0.5 ml) was added t-butylchlorodiphenylsilane (68 mg, 2 eq) in 0.5 ml DMF and the mixture stirred at 25° C. for 3 h. The solvent was then removed in vacuo and the residue chromatographed on silica gel (4:1 hexane/ether) to afford 68 mg of a 3:2 mixture of the desired TPS ether and t-butyldiphenysilanol, implying a yield of 90.4%.

β-anomer $^1$H NMR (200 MHz, CDCl$_3$): δ 7.7 (4H, m), 7.4 (6H, m), 5.02 (1H,dd,J=5.2, 2.0 Hz), 4.20 (1H,ddd,J=7.2, 7.1, 4.9 Hz), 4.02 (1H, m), 3.73 (2H, m), 3.25 (3H's,OMe), 2.26 (1H,ddd,J=13.4, 7.2, 2.0 Hz), 2.09 (1H,ddd,J=13.3, 7.1, 5.2 Hz), 1.09 (9H, s).

$^{13}$C NMR (50 MHz, CDCl$_3$): δ 135.6, 133.3, 129.8, 127.8, 104.7, 84.1, 64.6, 61.5, 55.1, 38.7, 26.8, 19.3.

α-anomer $^1$H NMR (200 MHz, CDCl$_3$): δ 7.7 (4H, m), 7.4 (6H, m), 5.07 (1H,dd,J=5.3, 1.1 Hz), 4.09 (2H, m), 3.75 (2H, m), 3.37 (3H's,OMe), 2.34 (1H, m), 2.05 (1H, m), 1.09 (9H,s).

The $^1$H NMR and $^{13}$C NMR of the mixture of anomers match the values reported in the literature for the separated anomers (Fleet).

EXAMPLE 8

D-β-3'-Azido-3'-deoxythymidine (D-AZT) and D-α-3'-Azido3'-deoxythymidine

Conversion of the silyl ether of Example 7 to D-AZT and its α-anomer was carried out by the method of Fleet with no changes.

EXAMPLE 9

(2S, 3S) 3-(2,2-Dimethoxyethyl)oxiranemethanol

To a solution of L-(+)-diisopropyl tartrate (0.962 g, 4.1 mmol) in dichloromethane (50 ml), cooled to −20° C., was added titanium tetraisopropoxide (1.2 g, 4.2 mmol), and the mixture stirred at −20° C. for 15 min. The allylic alcohol (0.6 g, 4.1 mmol) was then added as a solution in dichloromethane (10 ml) and after a further 10 min stirring at −20° C., t-butyl hydroperoxide (2.8 ml, 3.0 M, 2 eq) was added. The reaction mixture was stored in a refrigerator at -20° C. for 5 days and then quenched by addition of 30% NaOH in saturated sodium chloride. The mixture was allowed to warm to 25° C. and stirred a further 4 h, when MgSO$_4$ (3 g) and Celite (1 g) were added, and the resultant well-stirred mixture was filtered through a pad of Celite. After removal of the solvents in vacuo, the residue was chromatographed on silica gel (30:1; CH$_2$Cl$_2$/MeOH), yielding the epoxy alcohol (S, S) (491 mg, 75%) as a colorless oil.

$^1$H NMR (200 MHz, CDCl$_3$): δ 4.50 (1H,dd,J=6.5, 4.9 Hz), 3..82 (1H,dd,J=12.6, 2.5 HZ), 3.57 (1H,dd,=12.5, 4.4 Hz), 3.30 (3H's), 3.27 (3H's), 2.98 (1H, m), 2.96 (1H, m), 1.83-1.90 (1H, m), 1.69-1.79 (1H, m). 13C NMR (50 MHz, CDCl$_3$): δ 102.2 (d), 61.7 (t), 58.3 (d), 53.4 (q), 52.9 (q), 52.5 (d), 35.2 (t).

IR (neat): 3440, 2980, 2920, 2825 cm$^{-1}$.

EXAMPLE 10

(2R, 3R) 3-Azido-5,5-dimethoxypentane-1,2-diol

To a stirred mixture of the epoxy alcohol (S, S) (151 mg, 0.983 mmol) and azidotrimethylsilane (245 mg, 2.1 eq) in dichloromethane (10 ml) cooled to 0° C., was added diethylaluminum fluoride (2 ml, 25% solution 4 eq), and the mixture allowed to warm to 25° C. and stir a further 48 h. The reaction was quenched by addition of saturated NaHCO$_3$ (10 ml), the organic layer collected, and the aqueous layer washed with dichloromethane (2×10 ml). The combined organic extracts were washed with brine, dried over Na$_2$SO$_4$, filtered and the solvents removed in vacuo. The crude diol was chromatographed on silica gel (eluting first with CH$_2$Cl$_2$, then with 2% MeOH/CH$_2$Cl$_2$) yielding 116 mg {61%} of the pure azido diol.

$^1$H NMR (200 MHz, CDCl$_3$): δ 4.56 (1H,dd,J=11.1, 4.5Hz), 3.58-3.76 (3H, m), 3.44-3.5 (1H, m), 3.37 (6H, s), 1.95-2.05 (1H, m), 1.73-1.87 (1H, m). $^{13}$C NMR (50 MHz, CDCl$_3$): δ 102.3 (d), 73.5 (d), 63.2 (t), 60.4 (d), 53.8 (q), 53.5 (q), 33.9 (t), IR (neat): 3440 (v br), 2920, 2825, 2100 (N$_3$, sharp) cm$^{-1}$.

EXAMPLE 11

Methyl α- and β-L-3-Azido-2,3-dideoxyribofuranoside

To a solution of 14 mg (0.07 mmol) of the azido diol in dichloromethane (8 ml) at 25° C. was added 3 drops of approximately 1.5% HCl in aqueous MeOH, and the mixture stirred for 5 min. TLC showed complete conversion to a mixture of the anomeric products. The reaction was quenched by addition of 0.2 ml saturated aq. $NaHCO_3$ and vigorously stirred for 2 min. Sodium sulfate was added, the solution filtered, and the solvents removed in vacuo. Chromatography on silica gel (eluting first with $CH_2Cl_2$, then with 1% $MeOH/CH_2Cl_2$) yielded 10.1 mg (85%) of the pure mixture of the two anomeric products. Samples of the pure α or β anomer were obtained by either further silica gel chromatography or preparative TLC (eluting with 24:1 $CH_2Cl_2/MeOH$).

β-anomer $^1H$ NMR (200 MHz, $CDCl_3$): δ 5.10 (1H,dd,J=5.4, 1.7 Hz), 4.09–4.28 (2H, m), 3.78 (1H,dd,J=12 HZ), 3.63 (1H,m,J=8.9 Hz) 3.40 (3H's,OMe), 2.52 (1H,dd,J=9.0, 3.7 Hz, OH), 2.35 (1H,,ddd,J=13.9, 7.4, 1.8 Hz), 2.17 (1H,ddd,J=13.8, 6.4, 5.5 Hz).

α-anomer $^1H$ NMR (200 MHz, $CDCl_3$): δ 5.08 (1H,dd,J=5.2, 1.4 Hz), 3.84–4.02 (3H, m), 3.69 (1H, m), 3.39 (3H's,OMe), 2.40 (1H,ddd,J=14.1, 8.7, 5.3 Hz), 2.03 (1H,ddd,J=14.2, 3.6, 1.4 Hz), 1.82 (1H,dd,J=7.9, 4.6 Hz, OH).

mixture of α- and β-anomers $^{13}C$ NMR (50 MHz, $CDCl_3$): δ 105.2 (β), 104.9 (α), 85.2 (β), 82.3 (α), 63.5 (β), 62.2 (α), 60.6 (β), 59.8 (α), 55.6 (β), 55.1 (α), 39.5 (β), 39.1 (α). lit. (Fleet) $^{13}C$ NMR ($CDCl_3$): δ 105.1, 104.8, 85.2, 82.5, 63.5, 62.4, 60.6, 60.0, 55.5, 55.2, 39.5, 39.2.

IR (neat): 3250–3500 (ν br), 2925, 2100 (ν strong, sharp, $N_3$), 1435, 1365, 1325, 1255, 1100, 1040 $cm^{-1}$.

EXAMPLE 12

(2R, 3R) 3-Azido-5,5-dimethoxy-1-[(1,1-dimethylethyl)dimethylsilyloxy]-2-pentanol This compound was prepared from the azido-dideoxyribofuranoside of Example 11 by the normal method using t-butyl dimethysilyl chloride, 4-(dimethylamino)-pyridine, and triethylamine in dichloromethane. $^1H$ NMR (200 MHz, $CDCl_3$): δ 4.6 (1H,dd,J=4.1, 7.6 HZ), 3.71 (2H,d,J=3.5 Hz), 3.55 (2H, m), 3.368 (3H, s), 3.365 (3H, s), 2.62 (1H,d,J=5.0 Hz), 2.07 (1H,ddd,J=2.81, 7.5, 14.47 Hz), 1.66–1.80 (1H, m), 0.90 (9H, s), 0.095 (6H, s). IR (neat): 3445, 2940, 2920, 2840, 2100 ($N_3$), 1455, 1250 $cm^{-1}$.

What is claimed is:

1. A process for making a 2',3'-dideoxynucleoside of the formula (I)

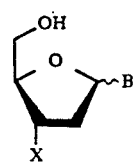

wherein X is H and B is a purine or pyrimidine base, comprising the steps of (a) converting a diol having the formula (II)

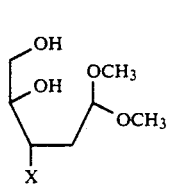

wherein X is H, to a dideoxyribofuranoside having the formula (III)

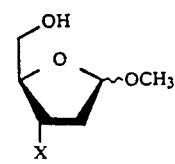

wherein X is H; and (b) coupling a purine or pyrimidine base to the dideoxyribofuranoside of formula III to obtain the 2',3'-dideoxynucleoside of formula I defined above.

2. A process as recited in claim 1, wherein the diol of formula II is converted to the dideoxyribofuranoside of formula III by treating the diol with dilute acid.

3. A process as recited in claim 1, wherein the step of coupling the purine or pyrimidine base to the dideoxyribofuranoside comprises substeps of (i) forming a hydroxy-protected dideoxyribofuranoside having the formula (IV)

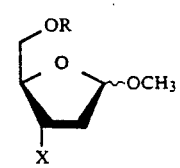

wherein X is H and R is a hydroxy-protecting group, (ii) reacting the hydroxy-protected dideoxyribofuranoside of formula IV with a silylated purine or pyrimidine base in the presence of a trialkylsilyl triflate, and (iii) removing the hydroxy-protecting group to obtain the 2',3'-dideoxynucleoside of formula I defined above.

4. A process as recited in claim 1, further comprising the step of separating the 2',3'-dideoxynucleoside of formula I into α and β anomers having the formulas Ia and Ib, respectively,

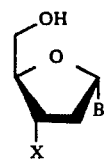

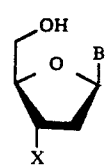

wherein X and B are as defined above.

5. A process as recited in claim 1, wherein X is H, and the diol of formula II is prepared by reacting an epoxy alcohol having the formula (V)

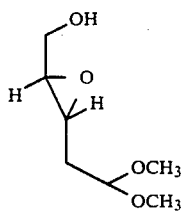

with diisobutylaluminum hydride.

6. A process as recited in claim 1, wherein B is thymine.

7. A process as recited in claim 1, wherein B is cytosine.

8. A process for making a 2',3'-dideoxynucleoside of the formula (I)

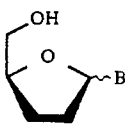

wherein B is a purine or pyrimidine base, comprising the steps of:
(a) reacting (1,3-butadien-1-yl)oxytrimethylsilane with trimethyl orthoformate to form 5,5-dimethoxypent-2-enal;
(b) reducing 5,5,-dimethoxypent-2-enal with diisobutylaluminum hydride to form 5,5-dimethoxypent-2-en-1-ol;
(c) forming (2R,3R) 3-(2,2-dimethoxyethyl)oxiranemethanol by Sharpless epoxidation of 5,5-dimethoxypent-2-en-1-ol;
(d) reacting (2R,3R) 3-(2,2-dimethoxyethyl)oxiranemethanol with diisobutylaluminum hydride to form 5,5-dimethoxypentane-1,2-diol;
(e) treating 5,5-dimethoxypentane-1,2-diol with dilute acid to form a 2,3-dideoxyribofuranoside having the formula II; and

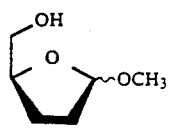

(f) coupling a purine or pyrimidine base to the dideoxyribofuranoside of formula II to obtain the 2',3'-dideoxynucleoside of formula I defined above.

* * * * *

UNITED STATES PATENT AND TRADEMARK OFFICE
CERTIFICATE OF CORRECTION

PATENT NO. : 5,220,003
DATED : June 15, 1993
INVENTOR(S) : Michael E. Jung; John M. Gardiner It is certified that error appears in the above-indentified patent and that said Letters Patent is hereby corrected as shown below:

On the title page

[56] References Cited, OTHER PUBLICATIONS, column 1, line 5, change "Fleet et al...Intermediate for the Synthesis of Substituted..." to -- Fleet et al...Intermediate for the Synthesis of 3'-Substituted... --.

[56] References Cited, OTHER PUBLICATIONS, column 2, line 1, change
"1-(2'Deoxy-$\beta$-D-lyxofuranoxyl)thymine," to
--1-(2'-Deoxy-$\beta$-D-lyxofuranosyl)thymine, --.

[56] References Cited, OTHER PUBLICATIONS, column 2, line 15, change
"Horwitz, eta l.," to
-- Horwitz, et al., --.

[56] References Cited, OTHER PUBLICATIONS, page 2, column 1, line 2, change
"fluoro-$\beta$-D-threopentofuranoxyl)cytosine" to
-- fluoro-$\beta$-D-threopentofuranosyl)cytosine --.

Column 1, line 35, after "1964," change "20" to -- 29 --.
Column 1, line 55, after "1986" insert a period.
Column 1, line 68, change "material" to -- materials --.

UNITED STATES PATENT AND TRADEMARK OFFICE
CERTIFICATE OF CORRECTION

PATENT NO. : 5,220,003
DATED : June 15, 1993
INVENTOR(S) : Michael E. Jung; John M. Gardiner It is certified that error appears in the above-indentified patent and that said Letters Patent is hereby corrected as shown below:

Column 2, lines 32,33, change
"3-azido-2,3-dideoyxribofuranoside" to
-- 3-azido-2,3-dideoxyribofuranoside --.
Column 2, line 1, change "thyine" to --thymine--.

Column 3, line 22, change
"2,,3,dideoxynucleosides" to
--2',3'-dideoxynucleosides--.

Column 4, line 9, after "mixture of" insert -- E --.
Column 4, line 10, after "desired" insert -- E --.
Column 4, line 35, change "2'3'" to -- 2',3' --.

Column 6, line 47, change "2'3'" to -- 2',3' --.
Column 6, 63, change "2'3'" to
-- 2',3' -- (both occurrences).

Column 7, lines 57,59, change "2'3'" to
-- 2',3' -- (both occurrences).
Column 7, line 67, after "enantio-DNA" delete the period.

Column 8, line 1, change "oxiranemthanol" to
-- oxiranemethanol --.

Column 9, line 41, change "10 855" to -- 10.855 --.
Column 9, line 58, change "(6H's)" to -- (6H,s) --.

UNITED STATES PATENT AND TRADEMARK OFFICE
CERTIFICATE OF CORRECTION

PATENT NO.  : 5,220,003
DATED       : June 15, 1993
INVENTOR(S) : Michael E. Jung; John M. Gardiner It is certified that error appears in the above-indentified patent and that said Letters Patent is hereby corrected as shown below:

```
Column 10, line 14, change "(6H's)" to -- (6H,s) --.
Column 10, line 42, change "3 57" to -- 3.57 --.
Column 10, line 43, change "(3H's)" to
          -- (3H,s) -- (both occurrences).
Column 10, lines 43, 44, change "1.69-1 79" to
          -- 1.69-1.79 --.
Column 10, line 53, change "1 26" to -- 1.26 --.
Column 10, line 65, change "64" to -- 64% --.
Column 10, line 67, change "H m" to -- H,m --;
          and change "(6H s)" to -- (6H,s) --.

Column 11, line 9,  change "25 ° C" to -- 25°C --.
Column 11, line 26, change "(3H's," to -- (3H,s, --.
Column 11, line 27, change "7 4" to -- 7.4 --.
Column 11, line 30, before "5.08" insert -- δ --.
Column 11, line 31, change "3 84-4.02" to -- 3.84-4.02 --,
          and change "(3H's," to -- (3H,s, --.
Column 11, line 60, change "(3H's," to -- (3H,s, --.
Column 11, line 67, change "(3H's," to -- (3H,s, --.

Column 12, line 34, change "3..82" to -- 3.82 --.
Column 12, line 35, change "(3H's)" to
          -- (3H,s) -- (both occurrences).
Column 12, line 37, change "13C" to -- $^{13}$C --.
Column 12, line 44, change "15I" to -- 151 --.
Column 12, line 56, change "{61%)" to -- (61%) --.
```

UNITED STATES PATENT AND TRADEMARK OFFICE
CERTIFICATE OF CORRECTION

PATENT NO. : 5,220,003
DATED : June 15, 1993
INVENTOR(S) : Michael E. Jung; John M. Gardiner It is certified that error appears in the above-indentified patent and that said Letters Patent is hereby corrected as shown below:

```
Column 13, line 19, change "(3H's," to -- (3H, s, --.
Column 13, line 20, change "(1H,," to -- (1H, --.
Column 13, line 25, change "(3H's," to -- (3H,s, --.
```

Signed and Sealed this

Twenty-fifth Day of April, 1995

Attest:

BRUCE LEHMAN

*Attesting Officer*    Commissioner of Patents and Trademarks